US006599254B2

(12) United States Patent
Winters

(10) Patent No.: US 6,599,254 B2
(45) Date of Patent: Jul. 29, 2003

(54) MULTI-FEATURE STEERABLE GUIDEWIRE FOR VASCULAR SYSTEMS

(76) Inventor: R. Edward Winters, One Launching Rd., Andover, MA (US) 01810

( * ) Notice: Subject to any disclaimer, the term of this patent is extended or adjusted under 35 U.S.C. 154(b) by 0 days.

(21) Appl. No.: 09/851,055

(22) Filed: May 8, 2001

(65) Prior Publication Data

US 2002/0095102 A1 Jul. 18, 2002

Related U.S. Application Data

(60) Provisional application No. 60/203,258, filed on May 8, 2000.

(51) Int. Cl.[7] .......................... A61B 5/00; A61M 25/00
(52) U.S. Cl. ...................................... 600/585; 600/434
(58) Field of Search ........................ 600/433, 434, 600/435, 585; 604/523, 529, 530, 264

(56) References Cited

U.S. PATENT DOCUMENTS

| 3,547,103 | A | * | 12/1970 | Cook | 600/585 |
| 4,922,924 | A | * | 5/1990 | Gambale et al. | 600/434 |
| 5,125,395 | A | * | 6/1992 | Adair | 600/104 |
| 5,402,799 | A | * | 4/1995 | Colon et al. | 600/585 |
| 5,429,139 | A | * | 7/1995 | Sauter | 600/434 |
| 5,951,496 | A | * | 9/1999 | Willi | 600/585 |
| 2002/0082523 | A1 | * | 6/2002 | Kinsella et al. | 600/585 |

* cited by examiner

*Primary Examiner*—Charles A. Marmor, II
(74) *Attorney, Agent, or Firm*—John M. Brandt

(57) ABSTRACT

A vascular system guidewire composed of a helically wound proximal spring segment attached to an additional helically wound distal spring segment of a more radiopaque material by winding the two segments together over a core. The helically wound springs may be tapered from the proximal to distal segment or straight, and a length of tubing is attached to the proximal end of the proximal spring segment with a ground distal tube segment to make for a flush fitting and a smooth continuous outside diameter of the guide wire. A core wire is attached to the end of the distal spring segment and moveable within the tube and proximal spring providing torque to the entire spring and movement of the core wire allows for varying the stiffness and support of the spring segment and for straightening the distal spring segment.

6 Claims, 2 Drawing Sheets

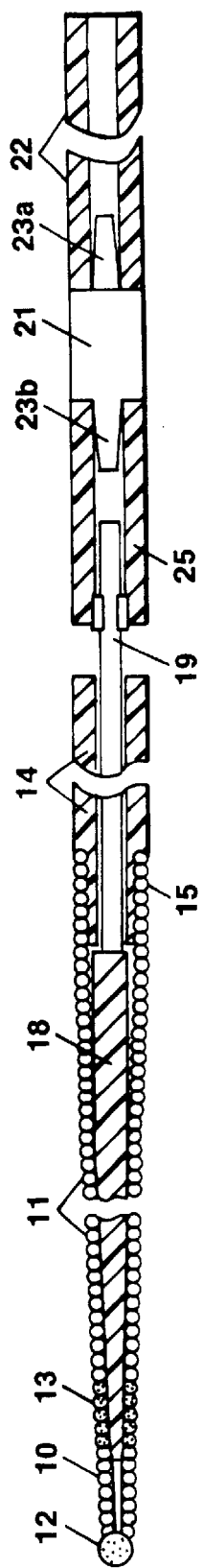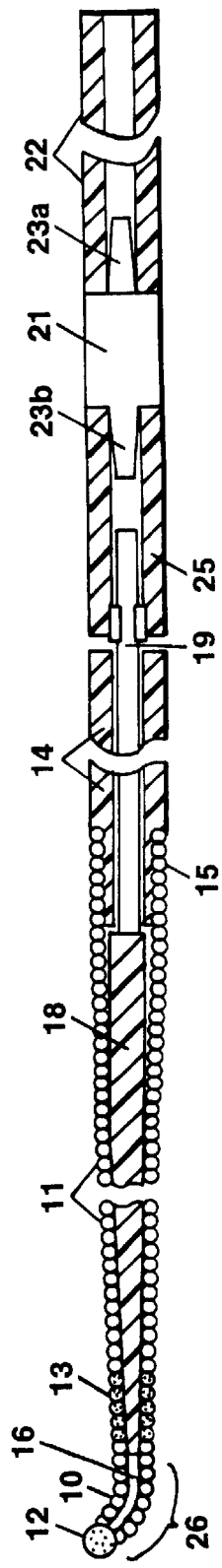

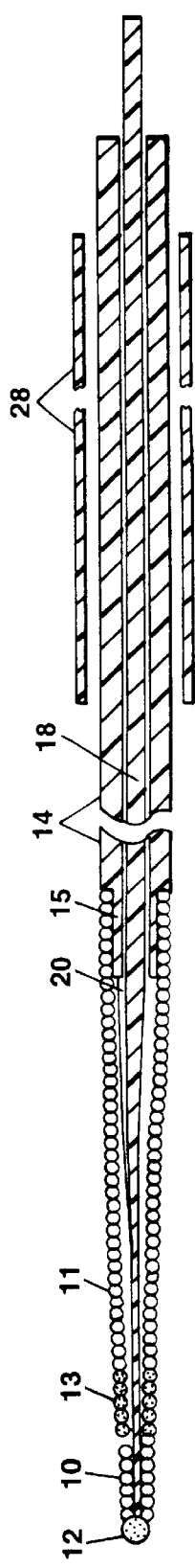
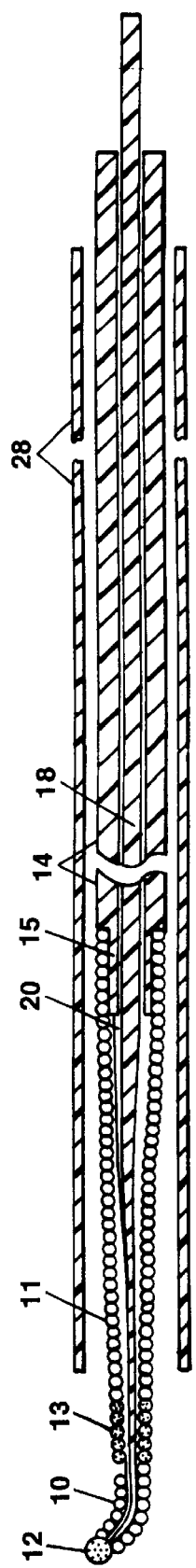
FIG. 2
FIG. 2a

MULTI-FEATURE STEERABLE GUIDEWIRE FOR VASCULAR SYSTEMS

CROSS REFERENCE TO RELATED APPLICATIONS

This application claims the benefit of the U.S. Provisional Application by the same inventor and of the same title, Ser. No. 60/203,258, filed May 8, 2000.

BACKGROUND OF THE INVENTION

1. Field of the Invention

The invention is related to guidewires used for the insertion of catheters into the vascular system or other internal body cavities such as the urethra, brain, biliary etc. as a method of treating disease or delivering a catheter or stenting device to open or hold open a segment of the vessel or pathway.

2. Description of the Prior Art

As a treatment technique for removing blockages in the vascular system, particularly those which affect the blood supply to the heart or brain, guidewires of very fine diameter are inserted directly into the system from outside the patient and manipulated or steered by the physician or practitioner through the system to the blockage by fluoroscopic observation. Since the various vessels through which the wire must pass are sinuous or irregular in shape and intersect and connect with other vessels at various and sometimes sharp angles, maneuvering the wire to the position of concern is a delicate task. The catheters designed for dilating or stenting these areas are generally not steerable devices and need to be advanced over a guide wire to locate the area desired.

Guide wires which are steerable are unlike standard guide wires which merely assist entering the body by providing a rail over which a catheter may be advanced for safely entering the pathway without scraping the surface they are entering. Steerable wires have the ability to be directed or torqued in order to direct the tip which has either a pre-formed tip or one formed by the user to match the requirements of the pathway. Once torqued in the desired direction they are advanced in the appropriate direction.

A plurality of guidewire type devices designed for this purpose exist in the prior art. Each is a novel approach to the problem of providing the user with sufficient control to transverse a pathway in a speedy and careful manner. For example, U.S. Pat. Nos. 4,545,390, Leary, and 3,789,841, Antoshkiw, both show distal tips formed of helically wound springs surrounding fixed tapered cores. U.S. Pat. No. 3,631,848, Muller, describes an axially movable distal tip extension tube of relatively short length.

A coil tip with tapered face edges which will curve toward the taper when pulled upon by an internal control wire is disclosed in U.S. Pat. Nos. 3,452,740, and 3,452,742, both to Muller. U.S. Pat. No. 4,650,467, Bonello shows a similar arrangement for inclining the tip by retraction of a control wire affixed thereto.

Additionally, U.S. Pat. No. 3,528,406, Jeckel et al. teaches the use of a fixed core wire having a reduced diameter in the spring tip portion of the wire. U.S. Pat. No. 3,625,200, Muller, discloses a curvable tip comprising solid cylindrical links engaging each other with ball and socket joints each of which is manipulatable by a fine core wire. U.S. Pat. No. 4,573,470, Samson shows a curved tip which is rotated in its entirety by rotating a core wire at the control handle.

Finally, U.S. Pat No. 4,783,983 teaches the use of a moveable core to straighten and stiffen the end of a steerable guide wire by advancing the core to the tip of the guide wire thus overcoming the bend of the safety wire.

The present invention is an improved guidewire which allows the user to vary the stiffness and support of the wire and vary the curvature of the tip from outside the patient during the transport and manipulation process by either retracting the core thus straightening a pre-formed tip segment, or in the case of the spring segment with restraining wire, advancing/pushing the core wire to force the distal segment to bend in one plane forming a curve the length of which is determined by the length of the spring being restrained and/or exposed past the end of the catheter or tube from which it extends.

SUMMARY OF THE INVENTION

The invention may be summarized as a guidewire of the type of and for the above described purpose consisting of a distal portion comprising two helically wound springs of differing material and the distal spring having a smooth rounded tip attached to the core, and a proximal portion comprising a length of tubing joined at the proximal end of the spring to form a continuous unit. A core wire tapered at the distal end is moveably disposed within the tubing and spring such that the amount of flexibility or floppiness of the spring may be varied by moving the core wire to various positions along the length, thus tensioning the distal spring segments. The distal core is swaged to allow for added flexibility while maintaining torque and for forming the distal tip segment to the desired curve and for eliminating the need for a separate safety wire to contain the coils whilst retaining flexibility and torque. When the core is advanced the distal tip may assume a curve as a result of the bias of the swaged core. With the core wire fully retracted the spring tip is straightened facilitating the penetration (crossing) of the lesion or partial blockage. A handle attached to the proximal tube segments allows for retracting or advancing the core and for imparting torque simultaneously to the guide wire tube or independently to the core thus torqueing either the entire guide wire or merely the distal spring segment thus avoiding the resistance to torque of the catheter through which the guide wire may be placed. To further facilitate crossing narrowings, the spring segment may be tapered forward of the tube segment.

Alternatively an additional smaller wire may be disposed within the tip end of the spring which prevents the spring coils from separating and allows a shape to be imparted to the tip when the core is advanced distally to tension the tip. The small wire is sufficiently thin to allow the tapered core wire to move freely within the spring segment. Thus with the core wire partially withdrawn, the end of the spring will straighten and stiffen as the core is attached to the distal spring coil. When the core is advanced the distal tip may assume a curve as a result of the tension on the swaged core forcing it to bend while being restrained by the smaller wire and surrounding spring segments. The design allows for a low profile device with sufficient strength to bend a catheter through which it is placed and to provide torque to the catheter for directing the catheter which has been bent in the desired direction.

These and other features and objects of the invention will become clearer from the following drawings and description of the preferred embodiment.

DESCRIPTION OF THE DRAWINGS

FIG. 1 is a cross sectional view of the preferred embodiment with the core retracted and the tip straight with increased column strength to provide more support since the coils are aligned and the core is under tension;

FIG. 1a is a cross sectional view of the preferred embodiment with the core not retracted or under tension thus allowing a pre-formed curve to be assumed in the swaged area of the core in the distal end of the spring segment;

FIG. 2 is a cross sectional view of the preferred embodiment with restraining wire in a relaxed state with the core retracted and the tip straight; and FIG. 2a is a cross sectional view of the preferred embodiment with the curve formed by advancing the core wire distally and thus forcing the end of the wire into a curve determined by the uncontained distal spring.

DESCRIPTION OF THE PREFERRED EMBODIMENT

Referring to FIGS. 1 and 1a and 2 and 2a, there is shown a cross sectional view of the steerable guidewire which comprises the preferred embodiment of the invention. Helically wound springs 10 and 11 composing the distal portion of the wire and joined by winding together at 13 are tapered outward from tip 12 toward tubing 14 and are only attached to core 18 at the distal end allowing free movement of the core within the spring segment. The amount or angle of taper and correspondingly the length of the coil are a matter of choice as dictated by clinical requirements and may be straight and equal in diameter to tube 14 thus providing a continuous smooth constant diameter transition between the tube and spring segments. A coil length of 30 centimeters has been found appropriate for intra-coronary applications and as will be obvious, the proximal portion of the coil may have little or no taper, the critical region being that nearest the tip for traversing tight narrowings. In the illustrated embodiment of FIGS. 1 and 1a and FIGS. 2 and 2a, the coil is substantially uniformly tapered. The distal spring 10 being of a more radio dense material for visibility under fluoroscopy or xray.

In FIGS. 1 and 1a and 2 and 2a is shown a swaged section of the distal segment 16 of core 18 which has sufficient rigidity to hold an imparted shape attached at the tip of spring 10 to provide bias for curving the tip and to prevent the coils of the spring from stretching apart.

As shown in FIGS. 1 and 1a and 2 and 2a, a core wire 18 is provided, which is substantially uniformly tapered forwardly to the core wire tip. Tapered core wire 18 is disposed within springs 10 and 11 and tubing 14 and extends as does tubing 14 a selected length to allow the user to place the core wire at various positions within the spring from outside the patient.

In FIGS. 1 and 1a, core 18 in addition to having the distal tapered segment, is ground down to fit within tube 14 such that the core 18 distal to the reduced diameter ground section 19 is too large to fit within tube 14 providing a stop for the core 18 when retracted, thus avoiding the potential of overstressing the distal core segment when fully retracted. A length of approximately 150 centimeters for the core has been found appropriate for this purpose.

FIG. 1a shows the attitude 26 that the tip will assume when the core is advanced or relaxed.

In FIG. 2 there is shown a cross sectional view of the steerable guidewire with restraining wire 20 and illustrates the wire in the relaxed mode with the core retracted straightening the spring tip. FIG. 2a illustrates the curved spring tip when the core is advanced and bent under tension due to the restraining wire and restraint of the outer spring segments 10 and 11. The overtube 28 in FIG. 2a allows for varying the radius of the curve formed by tensioning the core when advanced. Thus by lengthening or shortening the spring section outside of the overtube 28 the radius of curve formed may be adjusted to suit the application.

FIGS. 1 and 1a and 2 and 2a shows the tube 14 with ground section 15 to accommodate the proximal spring segment resulting in a uniform diameter over the spring and tube sections.

FIGS. 1 and 1a illustrates a dual tapered plug 21 which is rigidly attached at taper 23a to an extension tube 22 which is substantially the same as tube 14 but without a ground section. The ground tapered section 23b of the dual tapered plug 21 accommodates attachment to the tail tube 25 of the guide wire as illustrated in FIGS. 1 and 1a by forcing the tapered section 23b of the tapered plug 21 into the tail tube 25. The straight section of the tapered plug 21 is of the same diameter as tubes 22, 25 and 14 such that when forced together they form a continuous smooth constant diameter from the distal spring segment to the proximal end of the extension tube 22.

As is now evident, the invention disclosed herein allows a range of flexibility and control previously unavailable in the art. The wire of FIGS. 1 and 1a may be varied from a straight stiff configuration for penetrating or crossing lesions to a curved flexible profile of infinitely varying degree for steering through the junctions, twists and turns of the vascular system. When straightened and stiffened the wire provides greater column strength and support for a catheter to be advanced over the guide wire into the desired area. The wire of FIG. 2 and 2a likewise allows a range of flexibility and control unique to the design by allowing a very low profile control mechanism for tip deflection and torque to direct the wire or a catheter within which the wire is positioned into a desired area.

The materials of which the invention is constructed as well as the technique of use of the wire once in place to receive a catheter are well known and thus not herein described in detail. Similarly the control handle for holding the tubing and moving the core at the proximal end is a device of simple construction of the type described in the prior art. Accordingly, the invention is defined by the following claims

What is claimed is:

1. A steerable guidewire having a distal end and a proximal end comprising in combination:

a A first helically wound radiopaque spring having a distal end and a proximal end and an inside diameter and an outside diameter, said first spring constituting said distal end of said guidewire, said first spring shaped to a preformed curve;

b A second helically wound spring having a distal end and a proximal end disposed proximally of said first spring, said first and second springs joined at said proximal end of said first spring and said distal end of said second spring;

c A tube having a distal end and a proximal end and an inside diameter and an outside diameter, said tube disposed proximally of said second spring and joined to said second spring at said distal end of said tube and said proximal end of said second spring forming a juncture; and d A core wire of a diameter substantially equal to said inside diameter of said first spring at a distal portion of said core wire and attached to said distal end of said first spring at said distal portion of the core wire, said core wire moveable within said second spring and said tube wherein said first spring is straightened upon moving said core wire proximally and curved by moving said core wire distally.

2. The guidewire of claim 1 including means for limiting the travel of said core wire within said second spring and said tube.

3. The guidewire of claim 1 wherein said outside diameter of said second spring and said tube are equal at said juncture and wherein, at said juncture, a portion of said tube is of reduced diameter to fit within said second spring.

4. The guidewire of claim 1 further including a rounded tip disposed at said distal end of said first spring.

5. The guidewire of claim 1 further including an overtube surrounding said first and second springs to limit the curvature of said first spring.

6. The guidewire of claim 1 wherein said first spring is tapered toward said distal end.

* * * * *